United States Patent [19]

[11] 4,285,999

Olivieri et al.

[45] Aug. 25, 1981

[54] METHOD AND APPARATUS INVOLVING ADHESIVE BACKED PHOTOGRAPHS

[76] Inventors: Anthony Olivieri, 23 Quaker La., Dedham, Mass. 02026; Anthony Macrina, 47 Henry Ave., Melrose, Mass. 02176

[21] Appl. No.: 102,245

[22] Filed: Dec. 10, 1979

Related U.S. Application Data

[62] Division of Ser. No. 871,784, Jan. 24, 1978, Pat. No. 4,201,613.

[51] Int. Cl.3 .............................................. A61F 13/02

[52] U.S. Cl. ........................................ 428/40; 428/41; 428/202

[58] Field of Search .................................... 428/40–42, 428/202, 352; 156/268, 291, 289; 40/594; 206/633

[56] References Cited

U.S. PATENT DOCUMENTS

| | | | |
|---|---|---|---|
| 2,303,346 | 12/1942 | Flood | 156/268 X |
| 2,304,787 | 12/1942 | Avery | 156/268 X |
| 3,326,450 | 6/1967 | Langdon | 206/633 X |
| 3,949,935 | 4/1976 | Stackig | 428/42 X |
| 4,093,073 | 6/1978 | Leezer | 206/633 X |

*Primary Examiner*—David A. Simmons
*Attorney, Agent, or Firm*—Herbert L. Bello

[57] ABSTRACT

A pressure sensitive adhesive coating is applied to selected regions of one face of a release web, other regions of the one face being free of the adhesive coating. A photographic print is superposed on the release web face having the adhesive and the adhesive free regions, the back surface of the print contacting the adhesive coating. The release web is slit along a line that extends the length of the print and passes over the adhesive free regions. The slit forms a pair of tabs in the release web at the adhesive free regions. The tabs facilitate removal of the release web without bending of the photographic print.

10 Claims, 6 Drawing Figures

METHOD AND APPARATUS INVOLVING ADHESIVE BACKED PHOTOGRAPHS

CROSS REFERENCE TO RELATED APPLICATIONS

This application is a divisional application of Ser. No. 871,784, filed Jan. 24, 1978, now U.S. Pat. No. 4,201,613.

BACKGROUND OF THE INVENTION

1. Field of the Invention:

The present invention relates to photographic prints and, more particularly, is directed towards a method and apparatus for applying an adhesive backing to photographic prints.

2. Description of the Prior Art:

Various techniques and devices have been devised for mounting a variety of items. For example, labels are provided with a pressure sensitive adhesive backing onto which a split release paper is superposed. The pressure sensitive adhesive is exposed by first bending the label to enlarge the split opening and by then peeling back the release paper. The general concept of using a pressure sensitive adhesive backing on photographic prints is disclosed in U.S. Pat. No. 3,949,935 wherein small tabs with pressure sensitive adhesive are transferred from an envelope and pressed against the back of the print. In this case, the edges and corners of the prints are exposed to the potential risk of being bent and frayed. These disadvantages and that of curling could be overcome by covering the entire back surface of the photographic print with a pressure sensitive adhesive in the manner herein described for the label. However, covering the entire back surface of a photographic print with a pressure sensitive adhesive in the manner described in connection with the label suffers from certain disadvantages. For example, bending of the photographic print to remove the release paper may result in creasing of the print itself and marring of the picture.

SUMMARY OF THE INVENTION

It is an object of the present invention to provide a method and apparatus for producing an adherent backed photographic print which does not suffer from the heretofore mentioned disadvantages and limitations.

Another object of the invention is to provide an adherent backed photographic print with a release stratum having a pair of tabs for readily removing the release stratum and exposing an adhesive coating on the back surface of the photographic print so that the print can be applied instantly to a variety of surfaces and items such as albums, folders, official records, luggage, and the like.

Yet another object of the invention is to provide a method and apparatus for covering selected regions of one face of a release paper with a pressure sensitive adhesive coating, superposing the photographic print on the release paper so that the back surface of the print is in contact with the adhesive coating, and slitting the release paper to form a pair of tabs for readily removing the release paper and exposing the adhesive coating without bending the photographic print.

A further object of the invention is to provide a method and apparatus involving application of a pressure sensitive adhesive coating to certain regions on one face of a release web, certain other regions of the face being free of the pressure sensitive adhesive. A photographic print is superposed on the coated and uncoated surfaces of the release web, the back surface of the photographic print contacting the adhesive coating. The level of cohesion between the back surface of the photographic and the adhesive coating and the level of cohesion between the release web and the adhesive coating is such that the adhesive coating adheres to the back surface of the photographic print and the release web is readily removed from the adhesive coating. The release web is severed into two sections, a pair of tabs formed in the release web at the adhesive free areas. Since the tabs are not in contact with the pressure sensitive adhesive, they are easily pulled away from the back surface of the photographic print. The tabs constitute gripping members for removing the release web and exposing the pressure sensitive adhesive without bending the photographic print.

Other objects of the present invention will in part be obvious and will in part appear hereinafter.

The invention accordingly comprises the method and apparatus, together with their steps, parts, elements and interrelationships that are exemplifed in the following disclosure, the scope of which will be indicated in the appended claims.

BRIEF DESCRIPTION OF THE DRAWINGS

A fuller understanding of the nature and objects of the present invention will become apparent upon consideration of the following detailed description taken in connection with the accompanying drawings wherein.

DETAILED DESCRIPTION OF THE PREFERRED EMBODIMENTS

Figure 3:
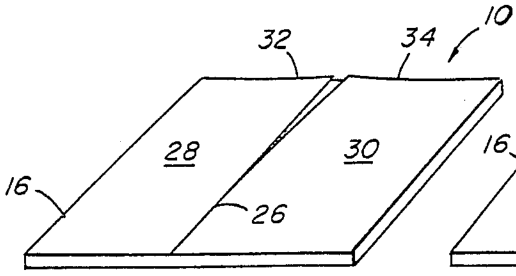
FIG. 3 is a perspective view of a laminated photographic print made in accordance with the present invention.
Figure 5:
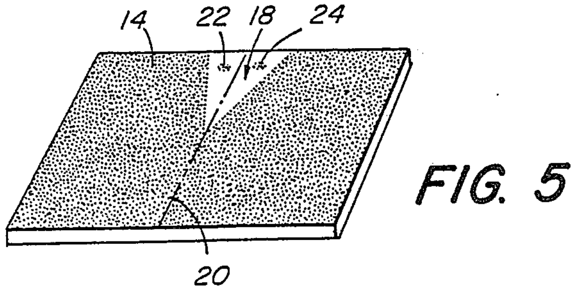
FIG. 5 is a perspective view of the photographic print of FIG. 3 with the release stratum removed.
Figure 6:
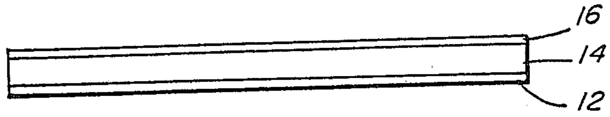
FIG. 6 is an end view of the laminated photographic print.

Referring now to the drawings, particularly FIGS. 3 and 6, an adhesive backed photograph 10 made in accordance with the present invention includes a processed photographic print 12 having a pressure sensitive adhesive layer 14 on certain areas of the back side thereof and a release web 16 superposed on the adhesive layer. As shown in FIG. 5, a substantially triangular area 18 disposed about a centerline 20 of the back surface of photographic print 12 is void of pressure sensitive adhesive 14. In the illustrated embodiment, a pair of pressure sensitive adhesive dots 22 and 24 are disposed equidistant from centerline 20 within triangular area 18. Pressure sensitive adhesive is applied to approximately ninety percent of the back or unfinished surface of photographic print 12 including all corners, approximately ten percent of the unfinished surfaces being free of adhesive.

Release web 16 is split at 26 to form approximately equal sections 28 and 30, the split being in substantial registration with centerline 20. The portions of release web 16 superposed on pressure sensitive adhesive layer 14 lightly adhere thereto and are readily removed. The portions of release web 16 superposed on adhesive-free area 18 does not adhere thereto and forms a pair of tabs 32 and 34 for readily removing the release web without bending photographic print 12. Pressure sensitive adhesive 22 and 24 hold tabs 32 and 34, respectively, against the back surface of photographic print 12 in order to avoid accidental exposure of pressure sensitive adhesive layer 14. When release web 16 is removed by pulling up on tabs 32 and 34, pressure sensitive adhesive layer 14 is exposed for mounting photographic print 12 on a variety of surfaces. An apparatus 40 for producing adhesive backed photograph 10 is shown in FIG. 1.

Figure 1:
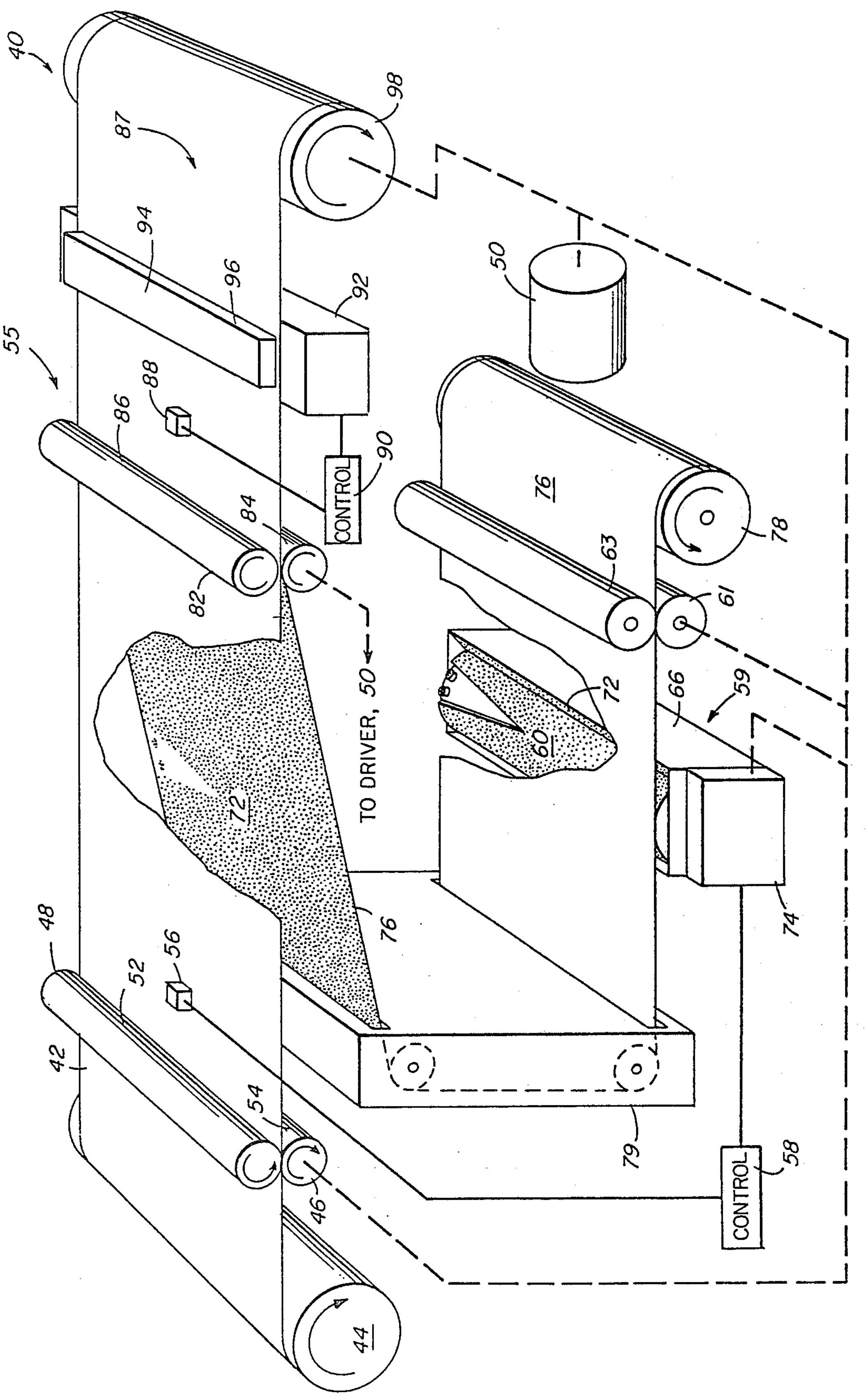
FIG. 1 is a schematic and block diagram of an apparatus emboyding the present invention.

Referring now to FIG. 1, an endless web of connected processed photographic prints 42 wound on a roll 44 is threaded between a driven capstan 46 and an idler roll 48. Capstan 46 is driven by a driver 50, for example an electric motor. Photographic prints 42 are wound on roll 44 in such a way that the finished surface of the print faces upwardly towards idler roll 48. In order to prevent marring of the finished photographic surface, capstan 46 and roll 48 are provided with napped coverings 52 and 54, for example felt covers. Drive capstan 46 and idler roll 48 rotate in such directions to advance photographic prints 42 towards a release web applying station 55 at which the photographic prints are superposed on an endless release web 76 having a pressure sensitive adhesive 72 applied to selected regions of one face thereof. Advancement of photographic prints 42 towards station 55 is detected by a sensor 56 which is connected to a controller 58 that actuates an adhesive applicator roll 60 at an adhesive applying station 59. Release web 76, which is wound on a roll 78 is engaged by a drive capstan 61 and idler roll 63 and is fed through adhesive applying station 59, wherein pressure sensitive adhesive 72 is applied to selected regions on one face of the release web. In one embodiment, sensor 56 detects the leading or trailing edge of each photographic print 42. In an alternative embodiment, photographic prints 42 are provided with coded indicia which is detected by sensor 56. Applicator roll 60 is rotated by a drive mechanism 74 at predetermined time intervals under the control of controller 58 so that the selected uncoated regions on the face of release web 76 correspond to a predetermined position on the back surface of photographic prints 42. Sensor 56 detects the presence of the advancing photographic print 42 and generates a command signal which is applied to controller 58. A command signal generated by controller 58 is applied to drive mechanism 74 for actuating the rotation of applicator roll 60 at the proper time to apply a pressure sensitive adhesive 72 in the manner shown in FIG. 5.

Figure 2:
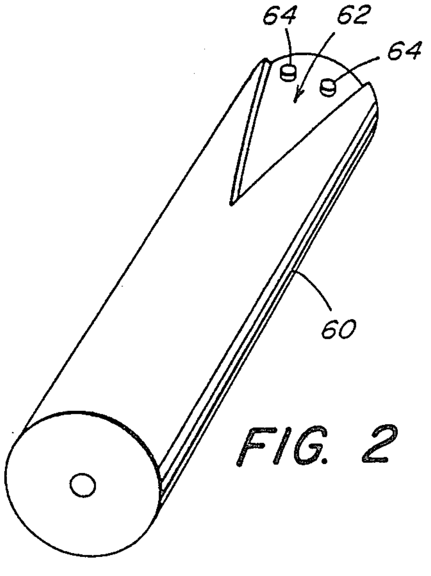
FIG. 2 is a perspective view of the adhesive applicator roller of FIG. 1.

As best shown in FIG. 2, applicator roll 60 includes a recessed portion 62 having a substantially triangular profile, for example. A pair of studs or pads 64 are disposed within recessed portion 62, the upper surface of the pads being flush with the upper surface of roll 60. Applicator roll 60 is mounted within a tank 66 containing pressure sensitive adhesive 72 in liquid form, for example a hot melt adhesive, an emulsified adhesive, or a solvent adhesive. The level of liquid adhesive 72 is such that only the outer surface of roll 60 and pads 64 contact the liquid adhesive, recessed portion 62 being out of contact with the liquid adhesive. The material of applicator roll 60 and pads 64 is such that it will transfer readily liquid adhesive 72 from the surface of the roll and the pads to release web 76. Obviously, the material of applicator roll 60 and pads 64 will not be adversely affected by liquid adhesive 72. After pressure sensitive adhesive 72 is applied to the selected regions of release web 76, the adhesive coated release web passes through an adhesive processor 79, for example an oven. Adhesive coated release web 76 exits oven 79 in such a manner that adhesive coating 72 faces the back or unfinished surface of photographic prints 42. Release web 76 has a release coating, for example a silicone release coating, having a low cohesion level with respect to adhesive 72.

Adhesive coated release web 76 and photographic prints 42 are threaded through a drive capstan 80 and an idler roll 82 at release web applying station 55, drive capstan 80 being connected to motor 50. Capstan 80 and roll 82 are provided with napped coverings 84 and 86, for example felt covers, for protection of the surfaces of photographic prints 42. Capstan 80 and roll 82 are operative to press photographic print against adhesive coating 72. The tackiness between the unfinished surface of photographic prints 42 and adhesive coating 72 is greater than the tackiness between release web 76 and adhesive coating 72. That is, the level of cohesion between the unfinished surface of photographic prints 42 and adhesive coating 72 and the level of cohesion between release web 76 and adhesive coating 72 is such that the adhesive adheres to the unfinished surface of the photographic prints and the release web is readily separated from the adhesive coating.

The advancing laminate of photographic prints 42, adhesive layer 72, and release web 76 moves towards a slitting station 87 and passes under a sensor 88 which detects the leading or trailing edge of each photographic print. Sensor 88 is connected to a controller 90 which actuates a slitter 92, for example a back splitter manufactured by Webtron, Inc. of Chicago, Illinois. Controller 90 synchronizes the actuation of slitter 92 with the advancement of photographic prints 42 for severing release web 76 at the centerline of each photographic print. Slitter 92 is operative to slit only release web 76 without marking photographic prints 42. In the illustrated embodiment, slitter 92 is provided with a backer 94 having a napped surface 96, such as felt on its underside, for protection of the finished surface of photographic prints 42. Slitter 92 slits release web 76 along a line that extends the length of print 42 and passes over adhesive-free area 18. After release web 76 is slit, the laminate of photographic prints 42, adhesive 72, and the release web is wound on a take-up roll 98. It is to be understood that the roll of adhesive-backed photographic prints is applied to a cutting mechanism (not shown) which separates the roll into individual prints.

From the foregoing, it will be readily appreciated that the method for producing an adhesive-backed photographic print embodying the invention includes the steps of applying a pressure sensitive adhesive to selected areas of a release web, superposing a photographic print on the applied pressure sensitive adhesive and slitting the release stratum to form tabs for readily removing the release stratum and exposing the pressure sensitive adhesive without bending the photographic print.

Figure 4:
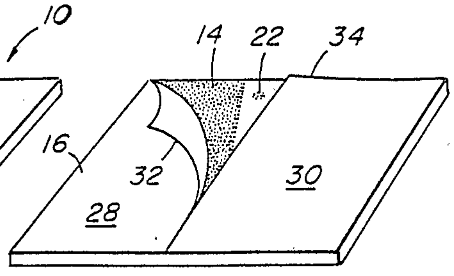
FIG. 4 is a perspective view of the photographic print of FIG. 3 with the release stratum partly removed.

In an alternative embodiment, the pressure sensitive adhesive is applied to certain areas of the unfinished surface of the photographic prints rather than to certain areas of the release web. That is, an alternate embodiment for producing an adhesive-backed photographic print includes the steps of applying a pressure sensitive adhesive to selected areas of the unfinished surface of a processed photographic print, superposing a release stratum on the applied pressure sensitive adhesive and splitting the release web to form tabs for readily removing the release web and exposing the pressure sensitive adhesive without bending the photographic print. In this case, the pressure sensitive adhesive, preferably an emulsified adhesive, is applied to the unfinished surface of the photographic print in such a manner that the adhesive-free areas are disposed about the centerline of the print and the release web is split along a line that passes over the adhesive-free areas as previously described and shown in FIGS. 3, 4 and 5.

Since certain changes may be made in the foregoing disclosure without departing from the scope of the invention involved, it is intended that all matter contained in the above description and depicted in the accompanying drawings be construed in an illustrative and not in a limiting sense.

What is claimed is:

1. An adhesive backed photographic print comprising:

(a) a processed photographic print having finished and unfinished surfaces on opposite faces;

(b) first pressure sensitive adhesive means on certain areas of said unfinished surface, the remaining area of said unfinished surface being free of adhesive;

(c) second pressure sensitive adhesive means in said adhesive free area on said unfinished surface, said second pressure sensitive adhesive means isolated from said first pressure sensitive adhesive means;

(d) a release web superposed on said first and second pressure sensitive adhesive means and on said adhesive free area, said release web having a pair of tabs adjacent said adhesive free area, said tabs defining gripping members for removing said release web and exposing said first and second pressure sensitive adhesive means, said second pressure sensitive adhesive means operative to hold said release web flat against said adhesive free area.

2. The adhesive backed photographic print as claimed in claim 1 wherein said release web is slit, said tabs formed at said slit.

3. The adhesive backed photographic print as claimed in claim 2 wherein said slit is disposed substantially along a centerline of said photographic print.

4. The adhesive backed photographic print as claimed in claim 3 wherein said adhesive free area is disposed about said centerline.

5. The adhesive backed photographic print as claimed in claim 4 wherein said adhesive free area has a substantially triangular profile and said second pressure sensitive means is a pair of pressure sensitive adhesive dots, one of each said dots disposed on one side of said centerline.

6. The adhesive backed photographic print as claimed in claim 4 wherein said second pressure sensitive adhesive means includes a pair of pressure sensitive patches disposed within said adhesive free area, said pressure sensitive patches disposed on opposite sides of said centerline.

7. An adhesive backed photographic print comprising:

(a) a processed photographic print having finished and unfinished surfaces on opposite faces;

(b) a release web; and (c) first and second pressure sensitive adhesive means on one face of one of said release web and said unfinished surface, an adhesive free area bounded by said first pressure sensitive adhesive means, said second pressure sensitive adhesive means separated from said first pressure sensitive adhesive means and bounded by said adhesive free area;

(d) said release web and said photographic print superposed on one another with said first and second pressure sensitive adhesive means sandwiched therebetween, the cohesion level between said unfinished surface and said first and second pressure sensitive adhesive means is greater that the cohesion level between said release web and said first and second pressure sensitive adhesive means, a portion of said release web constituting at least one tab for removing said release web and exposing said first and second pressure sensitive adhesive means, said second pressure sensitive adhesive means operative to hold said release web flat against said unfinished surface.

8. The adhesive backed photographic print as claimed in claim 7 wherein said release web is slit, said tab formed by said slit.

9. The adhesive backed photographic print as claimed in claim 7 wherein said second pressure sensitive adhesive means is a pair of patches disposed in said adhesive free area on said one of said faces of said release web and said unfinished surface.

10. The adhesive backed photographic print as claimed in claim 9 wherein said release web is slit along a centerline of said print, said adhesive free area disposed about said slit, one of each of said patches disposed about said centerline.

* * * * *